United States Patent [19]

Losi et al.

[11] 4,012,294

[45] * Mar. 15, 1977

[54] GOLD SULFITE BATHS CONTAINING ORGANOPHOSPHOROUS COMPOUNDS

[75] Inventors: Salvatore Losi, Geneva, Switzerland; Pierre LaLanne, Gex, France; Rene Henzi; Erwin Marka, both of Geneva, Switzerland

[73] Assignee: Oxy Metal Industries Corporation, Warren, Mich.

[ * ] Notice: The portion of the term of this patent subsequent to Sept. 9, 1992, has been disclaimed.

[22] Filed: Aug. 26, 1975

[21] Appl. No.: 607,742

Related U.S. Application Data

[62] Division of Ser. No. 386,798, Aug. 8, 1973, Pat. No. 3,904,493.

[30] Foreign Application Priority Data

Aug. 10, 1972 Switzerland ..................... 11975/72
Aug. 6, 1973 Switzerland ..................... 11388/73

[52] U.S. Cl. .......................... 204/43 G; 204/46 G
[51] Int. Cl.$^2$ ..................... C25D 3/48; C25D 3/62
[58] Field of Search ................ 204/43 G, 44, 46 G

[56] References Cited

UNITED STATES PATENTS

| | | | |
|---|---|---|---|
| 3,057,789 | 10/1962 | Smith | 204/46 G |
| 3,475,292 | 10/1969 | Shoushanian | 204/44 |
| 3,666,640 | 5/1972 | Smith | 204/44 |
| 3,672,969 | 7/1972 | Nobel et al. | 204/43 G |
| 3,883,409 | 5/1975 | Olivier | 204/44 |
| 3,904,493 | 9/1975 | Losi et al. | 204/43 G |

OTHER PUBLICATIONS

Sonya J. Westerback et al., Nature, vol. 178, pp. 321–322, Aug. 11, 1956.

*Primary Examiner*—G. L. Kaplan
*Attorney, Agent, or Firm*—Arthur E. Kluegel; Richard P. Mueller; B. F. Claeboe

[57] ABSTRACT

Disclosed is an improved gold-sulfite bath for plating gold and gold alloy deposits. By the inclusion in the bath of small amounts of certain organic phosphorus compounds, the quality of the deposit is rendered less sensitive to substantial changes in operating variables.

5 Claims, 7 Drawing Figures

GOLD SULFITE BATHS CONTAINING ORGANOPHOSPHOROUS COMPOUNDS

This is a division of application Ser. No. 386,798, filed Aug. 8, 1973, now U.S. Pat. No. 3,904,493.

The present invention concerns the use of organophosphorus compounds in sulfite baths for the electrodeposition of gold and gold alloys as additives for improving the performances and the operating conditions of said baths.

The invention also concerns the sulfite baths for the electrodeposition of gold and gold alloys which contain at least one of said organophosphorus compounds.

The invention also concerns the process of depositing coatings of gold and gold alloys by the electrolysis of gold and gold alloys sulfite baths containing said organophosphorus compounds.

In general, these organophosphorus additives will strongly limit, during the electrolysis, the influence on the quality of the deposits of the variations of some operating factors such as temperature, pH of the bath, current density, type and degree of agitation, etc.

It is well known in the art of electrodepositing gold and gold alloys from sulfite baths that the above onerating factors normally have a strong influence on the nature and the properties of the coatings obtained. Thus, it is often necessary to accurately control some of said factors in order to obtain deposits having the properties required (colour, ductility, gloss, etc.). Most often, relatively slight variations of current density result in the formation of foggy deposits, burns, pittings or colour changes, particularly when depositing gold alloys.

The introduction of said phosphorus compounds into sulfite gold baths largely prevents these difficulties. In the presence of such additives, it is possible to vary operational factors between relatively wide limits without affecting the quality of the coatings and, in case of gold alloys, without appreciably modifying the composition and the carat thereof. The principle of action of these additives is not known exactly; it is however possible that they may standardize the electrochemical properties of the various metals which are plated simultaneously, e.g. the electrodeposition potential and the distribution of ions in the cathode layer.

The present additives are stable water-soluble organic compounds of phosphorus of valency four or five comprising at least one P atom having up to four bonds identical or different chosen among PR and POR and having connected to the possibly free remaining valencies thereof substituents selected among O and OH free or salified with alkali metals, $NH_4^+$, earth-alkali metals or the metals which participate to the electrodeposition of the gold and its alloys.

The groups indicated by symbol R, identical or different, comprise monovalent or divalent organic radicals. In said second alternative. They can either be connected together in cyclic form or bridge with at least another phosphorus atom. R can denote the following substituents:

1. A linear, branched or cyclic aliphatic radical saturated or not which may comprise at least one function selected among halogens, CN, $NH_2$, CO, OH, COOH and $SO_3H$ free, as salts as mentioned above or esterified.

2. A mono- or polycyclic aromatic radical which can be substituted by linear, branched or cyclic aliphatic groups and which can comprise, as well as the substituent groups, at least one function like (1) above.

3. A radical as under (1) above further comprising at least one aromatic or heterocyclic substituent containing at least one N, O or S, said substituents themselves comprising or not functions as under (1) above.

4. A radical as under (1), (2) or (3) above which is interrupted by at least one N or O atom, the third valency of the N atom being connected to a hydrogen atom or to an organic rest.

5. A radical as described under 1) to 4) which is connected to a tetravalent P atom and a function of which having a labile proton is under anionic form to balance with the positive cationic charge of the phosphorus atom.

The number of carbon atoms of each substituent R is preferably comprised between 1 and 30 although this number can be exceeded in some cases.

Hence, among the compounds useful according to the present invention the following can be found:

a. Quaternary phosphonium compounds $R_4P^+X^-$, X being an anion derived from an organic or inorganic acid or an anionic function of one of the R groups (X can be derived for instance from $H_2SO_4$, HCl, $CH_3COOH$, $Cl_3COOH$, etc.).

b. Phosphine oxides $R_3PO$.

c. Phosphonic acids $RPO(OH)_2$ free, mono- or di-esterified.

d. Phosphinic acids $R_2PO(OH)$ free or esterified.

e. Organic phosphates $ROPO(OH)_2$, $(RO)_2PO(OH)$ and $(RO)_3PO$.

Naturally, compounds will also be found which are similar to the above but which have some of their substituents R connected to at least one second P atom substituted symmetrically or not symmetrically with the first one.

The phosphorus compounds which are preferably used as additives in sulfite baths for the electrodeposition of gold and gold alloys are phosphonic acids, phosphinic acids or mixed phosphono-phosphinic acids, their salts and their ester derivatives. Consequently, they can comprise one or several phosphorus atoms and the acid functions thereof can be free, salified or esterified partially or completely. If has been found that in many cases phosphoric and phosphonic esters are as active or more active than the corresponding free acids when added to the present gold baths and this observation is very surprising and completely unexpected. Indeed, if, as it is generally supposed, the activity of the free acid additives is due to the affinity between the acid OH functions and the metal ions dissolved in the bath, it is difficult to understand how the ester functions which should be relatively inert can even be more active. It should also be noted that the halogen and carbonyl derivatives of the present organo-phosphorus compounds are particularly active.

The present additives can be classified in a more detailed manner as follows:

1. Compounds containing one phosphonic group of formula (1)

wherein A represents a linear, branched or cycle containing alkyl or aralkyl hydrocarbon chain saturated or not comprising from 1 to 30 C atoms some of which may be substituted with one or several substituents selected among OH, ON, halogens (Cl, Br or I), COOH or $SO_3H$ groups free, salified or esterified, $NR^1R^2$ groups and oxygen (carbonyl groups). In addition, chain A may have inserted in the main part thereof or in the side branches one or several hetero-functions, e.g. O and $NR_3$. $R^1$ and $R^2$ are selected among hydrogen and linear or branched alkyl radicals halogenated or not having 1 to 6 C atoms, e.g. $CH_3$, $C_2H_5$, $C_3H_7$, iso-$C_3H_7$, $ClCH_2$, $ClCH_2$-CHCl, $(ClCH_2)_2$-CH, etc., $CH_2COOH$ and $CH_2SO_3H$ free, salified or esterified. Furthermore, $R^1$ and $R^2$ can constitute together with the N atom a 5 to 6 links heterocycle. $R^3$ has the same meaning as $R^1$ or $R^2$ but also comprises alkylene bridges connected to a possible second N atom of A.

2. Compounds having at least two phosphonic groups of formula $(HO)_2PO\text{-}B\text{-}PO(OH)_2$     (2)

wherein B represents a $C_1$ to $C_{30}$ linear, branched or cycle containing alkylene or aralkylene hydrocarbon chain saturated or unsaturated which may be substituted with one or several substituents selected among OH, CN, halogens (Cl, Br or I), acid groups such as COOH, $SO_3H$ or $PO_3H_2$ free, salified or esterified, $NR^4R^5$ groups and oxygen (carbonyl groups). In addition, chain B can be interrupted or not by one or several hetero-functions, e.g. O and $NR^6$. $R^4$ and $R^5$ represent the same substituents as $R^1$ and $R^2$ but further comprise a $(CH_2)_mPO_3H_2$ group free, salified or esterified ($m = 1$ or 2). $R^6$ comprises the same substituents as $R^3$ and, in addition, a $CH_2PO_3H_2$ group free, salified or esterified.

3. Compounds having at least two phosphonic groups of formula $(HO)_2OP\text{-}CR'R''\text{-}PO(OH)_2$     (3)

wherein R' represents a halogen (Cl, Br of I) or an OH (free or etherified); R'' represents H, halogens or $C_1$ to $C_6$ linear or branched alkyl or alkenyl groups which may be substituted or unsubstituted by at least one group selected among OH, CN, halogens (Cl, Br or I), acid groups such as COOH, $SO_3H$ and $PO_3H_2$ free, salified or esterified and oxygen.

4. Phosphinic and phosphono-phosphinic compounds of formulae similar to (1), (2) and (3) above but wherein the OH function of at least one of the phosphorus atoms is replaced by a group A' the definition of which is the same as for A above. Thus, examples of formulae of type (4) will be as follows:

HOPOAA'    HOPO—B—PO(OH)$_2$    (HO)$_2$PO—CR'R''—PO(OH)
                    |                                       |
                    A'                                      A'
(4:1)      (4:2)           (4:3)

wherein A, B, R' and R'' are defined as above and A' is preferably a linear or branched alkyl radical which may or not be substituted by halogens (Cl, Br or I), OH or $NR^1R^2$, $R^1$ and $R^2$ being defined as above.

5. Phosphono-phosphinic compounds of formula similar to (2) above wherein chain B is interrupted by one or several HOPO groups.

In the above compounds the ester and ether functions are preferably derived from lower alkanols which may be halogenated or not, e.g. methanol, ethanol, propanol, isopropanol, butanol, isobutanol, $ClCH_2OH$, $Cl_2CHOH$, $ClCH_2$—$ClCHOH$, $(ClCH_2)_2$—CHOH, etc.

A number of organophosphorus compounds which are useful according to the invention are listed below as non limitative examples. In the formulae of these compounds the acid functions have been generally represented in the free state but it is understood that such functions can actually be salified or esterified as mentioned above. This list of compounds which is far from being exhaustive is followed by references relative thereto, e.g. to the preparation thereof. Some of these references also comprise other compounds which can be used according to the invention and which are in accord with formulae (1) to (5) above. Generally, when the present compounds were initially obtained as esters, the latter were hydrolized by usual means, e.g. by boiling with aqueous mineral acid or alkali. However, in some cases, for instance with compounds having a P-CO bond some breakage of that bond occurred during hydrolysis, in which case the ester was preferably used as an additive in gold electroplating baths. Free acidic functions were esterified by usual means, e.g. by boiling with an alcohol in the presence or in the absence of a catalyst such as $H_2SO_4$, HCl, $BF_3$, etc.

Since the following list of compounds is not exhaustive, it will be understood that analog, homolog and other compounds similar to those outlined can also be useful according to the present invention.

Compounds of formula (1)

| | |
|---|---|
| $CH_3$—CHOH—PO(OH)$_2$ | HOCH$_2$—PO(OH)$_2$ |
| HOCH$_2$—CH$_2$—PO(OH)$_2$ | HOC(CH$_3$)$_2$—PO(OH)$_2$ |
| H$_5$C$_2$—CHOH—PO(OH)$_2$ | (CH$_3$)$_2$CH—CHOH—PO(OH)$_2$ |
| HOCH$_2$—CHOH—CH$_2$—PO(OH)$_2$ | HOCH$_2$(CHOH)$_5$—PO(OH)$_2$ |
| HOCH$_2$—CO—CH$_2$—PO(OH)$_2$ | H$_3$C—PO(OH)$_2$ |
| H$_5$C$_2$—PO(OH)$_2$ | (H$_3$C)CH—PO(OH)$_2$ |
| CH$_2$=CH—CH$_2$—PO(OH)$_2$ | C$_6$H$_5$—CH$_2$—PO(OH)$_2$ |
| ClCH$_2$—CH$_2$—PO(OH)$_2$ | Cl$_2$CH—PO(OH)$_2$ |
| Cl$_3$C—CHOH—PO(OH)$_2$ | ClCH$_2$—C(CH$_3$)OH—PO(OH)$_2$ |
| BrCH$_2$—CH$_2$—CH$_2$—C(CH$_2$Cl)OH—PO(OH)$_2$ | |
| ClCH$_2$—C(CH$_2$Cl)OH—PO(OH)$_2$ | Cl$_2$CH—C(CH$_2$Cl)OH—PO(OH)$_2$ |
| NC—CH$_2$—PO(OH)$_2$ | NC—(CH$_2$)3—PO(OH)$_2$ |
| H$_2$N—CH$_2$—PO(OH)$_2$ | CH$_3$NH—COCH$_2$—PO(OH)$_2$ |
| H$_6$C$_5$CO—NHCH$_2$—PO(OH)$_2$ | (HOCH$_2$CH$_2$)$_2$N—CH$_2$—PO(OH)$_2$ |
| (H$_5$C$_2$)$_2$N—CH$_2$—PO(OH)$_2$ | |
| (HO)$_2$OP—CH$_2$—COOH | |
| |  |
| (HO)$_2$OP—CHOH—COOH | |
| (HO)$_2$OP—CH(CH$_3$)—NH—CH$_2$—CH$_2$—NH$_2$ | |
| (HO)$_2$OP—C(CH$_3$)OH—COOH | (HO)$_2$OP—CH(COOH)$_2$ |
| CH$_3$—CO—PO(OH)$_2$ | H$_5$C$_2$—NHCO—PO(OH)$_2$ |

Compounds of formula (2)

$(HO)_2OP-CH_2-CHOH-CH_2-PO(OH)_2$
$(HO)_2OP-CH_2-PO(OH)_2$
$(HO)_2OP-(CH_2)_3-PO(OH)_2$
$(HO)_2OP-CH_2-CO-CH_2-PO(OH)_2$
$(HO)_2OP-CH_2-NH-CO-NH-CH_2PO(OH)_2$
$[(HO)_2OPCH_2]_2N-CH_2-CH_2-N[CH_2PO(OH)_2]_2$ in which at least one of the acid functions is esterified $(HO)_2OPCH_2-N-CH_2-CH_2-N-CH_2PO(OH)_2$
$\qquad\qquad |\qquad\qquad\qquad |$
$\qquad\quad CH_2COOH\qquad CH_2COOH$ $[(HO)_2OPCH_2]_2N(CH_2)_6-N[CH_2PO(OH)_2]_2$ $(HO)_2OPCH_2-N-CH_2-CH_2N[CH_2PO(OH)_2]_2$
$\qquad\qquad |$
$\qquad\quad CH_2CH_2OH$ $(HO)_2OP-CH(NH_2)-PO(OH)_2$ $(HO)_2OP-CH-PO(OH)_2$
$\qquad\quad |$
$\qquad\; CH_3$

$(HO)_2OPCH_2-N\diagup\diagdown N-CH_2PO(OH)_2$ $(HC)_2OP-CH=CH-PO(OH)_2$
$(HO)_2OP-CHOH-C_6H_4-CHOH-PO(OH)_2$
$(HO)_2OP-CH_2-C[PO(OH)_2]_2$
$\qquad\qquad\qquad |$
$\qquad\qquad\quad OH$ $(HO)_2OPCH_2-CCl_2-CH_2PO(OH)_2$
$(HO)_2OP-CH-PO(OH)_2$
$\qquad\quad |$
$\qquad\; CH_2COOH$
$(HO)_2OP-CHOH-(CH_2)_2-CHOH-PO(OH)_2$
$(HO)_2OP-CHOH-CH_2-CHOH-PO(OH)_2$
$(HO)_2OPCH_2-N(C_6H_{10}OH)-CH_2PO(OH)_2$
$(HO)_2OPCH_2-N(C_6H_4COOH)-CH_2PO(OH)_2$
$(HO)_2OP-COH-COH-PO(OH)_2$
$\qquad\quad |\qquad\; |$
$\qquad\; C_2H_5\; C_2H_5$
$(HO)_2OP-COH-PO(OH)_2$
$\qquad\quad |$
$\qquad\; CH_2-CH_2OH$ $(HO)_2OP-CH_2-CH_2-PO(OH)_2$
$(HO)_2OP-2-O-CH_2-PO(OH)_2$ $(HO)_2OP-C(NH_2)-PO(OH)_2$
$\qquad\quad\; |$
$\qquad\quad C_2H_5$ $(HO)_2OP-CO-PO(OH)_2$ $(HO)_2OP-C(CH_3)_2-PO(OH)_2$ Compounds of formula (3)

$(HO)_2OP-CHCl-PO(OH)_2$ $(HO)_2OP-CHOH-PO(OH)_2$
$(HO)_2OP-CCl_2-PO(OH)_2$
$(HO)_2OP-COH-PO(OH)_2$
$\qquad\quad |$
$\qquad\; CH_3$
$(HO)_2OP-COH-PO(OH)_2$
$\qquad\quad |$
$\qquad\; C_2H_5$
$(HO)_2OP-COH-PO(OH)_2$
$\qquad\quad |$
$\qquad\; CH_2-CH_2-COOH$
$(HO)_2P-COH-PO(OH)_2$
$\qquad\; |$
$\quad\; CH_2-CH_2-CO-CH_3$ $(HO)_2OP-CCl-PO(OH)_2$
$\qquad\quad |$
$\qquad\; C_2H_5$ $(HO)_2OP-CHBr-PO(OH)_2$
in which at least one of the acid functions is esterified $(HO)_2OP-COH-PO(OH)_2$
$\qquad\quad |$
$\qquad\; C_3H_7$
$(HO)_2OP-COH-PO(OH)_2$
$\qquad\quad |$
$\qquad\; CH_2-CH_2CN$
$(HO)_2P-COH-PO(OH)_2$
$\qquad\; |$
$\quad\; CH_2-CHCl_2$ Compounds of formula (4)

$(HOOC)_2PO(OH)$
$(CH_3)_2PO(OH)$
$(CH_3)_2COH-PO(OH)-CHOH-CH_3$
$H_9C_4-PO(OH)-COH-PO(OH)_2$
$\qquad\qquad\qquad |$
$\qquad\qquad\quad CH_3$ $(HOOC-CH_2)_2PO(OH)$
$(HOCH_2)_2PO(OH)$

Compounds of formula (4)

$CH_3PO(OH)-COH-PO(OH)CH_3$
$\qquad\qquad\quad |$
$\qquad\qquad CH_3$

-continued

| Compounds of formula (5) |
| --- |
| $(HO)_2OP-CH_2-PO(OH)-CH_2-PO(OH)_2$ |
| $(HO)_2OP-CHCl-PO(OH)-CHCl-PO(OH)_2$ |

| (6) Other compounds |
| --- |

References: (references to "Chemical Abstracts" are indicated C.A.)

G. M. KOSOLAPOFF: Organophosphorus Compounds, John Wiley & Sons, Inc., New York (1958)
Liebigs Ann. 707, 35-43 (1967)
Bull. Soc. Chim. 1967 (4), 1345-53; 4186
Ber. Deutsch. Chem. Gesell. 100 (5), 1571-4 (1967); 57, 1023 (1924
Monatsh. Chem. 99 (1), 166 (1968)
J. Phys. Chem. 71, 4194 (1967)
J. Am. Chem. Soc. 78, 4453, 4455 (1956)

C.A. 68, 24798; 68, 6882; 68, 95891; 67, 73652; 67, 43887; 67, 11549; 52, 241b; 50, 3993; 52, 7127d; 50, 11230g; 50, 10760g; 52, 3667; 51, 10366h.

South-Africa Pat. No. 6304,071.

U.S. Pat. Nos. 3,309,342; 3,322,863; 3,314,957; 3,303,139; 3,351,558; 3,344,077; 3,372,209; 3,346,487; 3,497,313; 3,297,796.

French Pat. Nos. 1,458,492; 1,458,566; 1,412,865; 1,134,796.

Dutch Pats. or published patent applications Nos. 66,10762; 65,14133; 66,06548.

German Pats. or published patent applications Nos. 1,232,142; 1,943,577; 1,194,852; 1,235,836.

Belgian Pat. Nos. 672,205; 619,619.

British Pat. Nos. 941,706; 703,180; 703,381; 744,633.

Sulfite baths for the electrodeposition of gold and gold alloys in which the present additives are particularly useful are known from the men skilled in the art. Such baths are described for instance in Swiss Pat. No. 506,628 and British Pat. No. 1,134,615. These baths contain the gold as a sulfite of gold or a gold sulfite complexed with an amine, the concentration of which can vary, for instance from 0.5 to 30 g of metal /1. They generally contain alkali or ammonium sulfites the quantity of which can vary from 1 to 150 g/1, chelateing or complexing agents such as water-soluble organic acids and hydroxyacids, e.g. citric, lactic, gluconic, tartaric, malic and acetic acids, corresponding alkali or ammonium salts and di- or polyamines. A series of such amines can be found for instance in "Modern Coordination Chemistry" by J. LEWIS & R. G. WILKINS, Intersc. Publ. New York, page xiii and comprises for instance ethylene diamine (en), ethylene diamine tetraacetic acid (EDTA) and diethylenetriamine pentaacetic acid and their alkali and ammonium salts. The amount of said additives is not critical and essentially depends on the bath compositions and the particular use thereof. Generally, concentrations between 0.1 g and 100 g/1 of such ingredients are possible. These baths can also contain various metal ions operating as brightening agents, e.g. Ni, As, Sb and Se, or being codeposited in larger amounts with the gold to form gold alloys. As such metals, the following ones can be mentioned: Fe, Co, Ni, Zn, Cd, Sn, Cu, Bi, Ga, In, Pb, Mn, Mo, Ag, Tl, Zr, V, W and, in some cases, the precious metals of the platinum group. Said metal ions are introduced into the present baths as water-soluble salts, chelates or complexes well known in the electroplating art (see for example "The Metal Finishing Guidebook Directory", Metals and Plastics Publ., Inc., Westwood, N.J., U.S.A.). The sulfates, sulfites, citrates or carbonates of said metals, complexed or not with the above described complexing agents, are used preferably when soluble in water. The amount of said metals in the present baths can vary between wide limits depending on the composition and the carat of the alloys to be plated. It can be comprised, for instance, between 0.5 and 150 g/1. However, these limits are not critical and it is possible to have concentrations below or above said limits in some cases. Thus, when the metals are used only as brightening agents, very small quantities can be effective, e.g. in the order of only 1 to 500 mg/1.

The present baths can also contain mineral or organic acids and bases as well as buffers so that the pH can be maintained between operating limits according to usual means. Examples of such acids are $H_2SO_4$, HCl, $H_2SO_3$, HCOOH and others. Examples of such bases are NaOH, KOH, LiOH and others. Examples of such buffers are citrate, borate and phthalate buffers. The pH of said baths are generally comprised between about 5 and 11; however, a given bath may have rather narrow operative pH limits.

The sulfite baths for the electrodeposition of gold and gold alloys operate at current densities generally comprised between rather narrow limits. For instance, in the case of a typical sulfite gold-copper bath, the optimal current density at 60° C is about 1 A/dm$^2$; in such case; it is not advisable to operate at densities 20% more or less than the average value as defective coatings might be produced (burns or alloy composition variations).

In contrast, in the presence of some of the additives used according to the invention, it is possible to operate at ± 50%, or better, of the medium density value without changes in the aspect and the properties of the deposited alloy. In some favourable cases, this interval can be even wider. Therefore, the importance of other operating factors closely related to the bath conductivity and consequently to current density are strongly minimized, e.g. temperature, pH, concentration of conductivity improving agents, type and strength of agitation, distance between anodes and the parts to be plated, etc. Generally, the addition of these organo-phosphorus compounds into the present baths permits obtaining deposits having reproducible and constant properties even in the case of relatively important variations in the operation parameters.

The effective quantities of the compounds useful according to the invention can vary between wide limits. These quantities depend, naturally, on the chemical structure of the phosphorus compound considered, that is on the nature and the number of the functional groups and, presumably, on their orientation. In some cases, a few mg/l, e.g. 1 to 2 mg/l are sufficient; in other cases higher concentrations, e.g. of the order of 10 to 100 g/l or even up to the limit of solubility in the bath can be desirable and advantageous.

The present additives can be incorporated to the baths, depending on the case, as the pure substances or as ready prepared solutions in water or water-soluble liquids such as alcohol, acetone or others.

When the non esterified forms of the present additives are used, it is generally immaterial that they should be added into the baths as the free acids or as the alkali salts thereof with the condition, of course, that the final pH of the bath be adjusted to the required value with an acid or a base, e.g. $H_2SO_4$ or NaOH.

Table 1 below shows the composition of a few sulfite gold and gold alloy baths wherein the present organo-phosphorus additives are very useful.

samples have been electrolytically coated in said baths with gold alloy deposits under the conditions indicated hereinbelow. Then, the experiment was repeated using the same bath composition but comprising a known amount of an organo-phosphorus additive. Thereafter, the differences between the test samples and the control samples with regard to plated surface aspect and properties were noted.

EXAMPLES 1 to 18

A sulfite bath for the electrodeposition of an Au—Cu—Cd alloy having a white to yellow-white colour was prepared by mixing the following ingredients at the concentrations indicated. EDTA means ethylene diamine tetraacetic acid or the alkali salts thereof.

| Ingredients | Concentration |
|---|---|
| Au (as gold sulfite) | 6 g/l |
| Cd (as EDTA complexed sulfate) | 12 g/l |
| Ni (as EDTA complexed sulfate) | 3 g/l |
| Cu (as EDTA complexed sulfate) | 0.06 g/l |
| EDTA (free) | 30 g/l |
| $Na_2SO_3$ | 30 g/l |
| pH (NaOH) | 9.7 – 1.0 |

The above bath (control bath) was purified with active charcoal according to usual means several hours before use.

The electroplating experiments were carried out under the following conditions: Temperature 57°–60° C; current density 0.5 A/dm²; weak to medium agitation; time sufficient for obtaining 20u thick deposits or more.

It was noted that with the control bath the above operating conditions could be varied only very slightly without experiencing difficulties. Indeed, when the current density was increased 0.1 or 0.2 A/dm² (that is up to 0.6 or 0.7 A/dm²), the platings started to burn. In addition, the levelling action was poor, that is the ac-

TABLE 1

GOLD AND GOLD ALLOYS SULFITE BATHS

Concentrations in g/l; concentrations of the alloy metals in g of metal /l

| Ex. | Au | Cd | Ni | Zn | Cu | Sb | Organic acid | alkali sulfite | Rochelle salt | en | chelatant of type EDTA | pH ** | t° C | Current density A/dm² |
|---|---|---|---|---|---|---|---|---|---|---|---|---|---|---|
| A) | 10 | | | | 20 | | 50 | 10 | | 50* | 60 | 6.5–6.8 | 60 | 0.8–1.2 |
| B) | 8–35 | 4 | | | | | 15 | 20 | | | 40⁺, 10⁺⁺ | 9.5–10 | 58 | 1.5 |
| C) | 8–30 | | | | 0.1 | 0.3–1 | 20–50 | 100 | 20 | 80* | 2–5 | 7.0–7.5 | 65 | 0.8–1.0 |
| D) | 3–10 | 15 | 6 | | | | | | | | 100 | | | |
| E) | 3–8 | 17 | 5–10 | | 0.2 | | | | | | 100 | | | |
| F) | 6 | 12 | | 5 | | | | | | | 100 | | | |
| G) | 6 | 12 | | 5 | 0.05 | | | | | | 100 | | | |

The above baths further contain 0.2 to 5 g/l of one or several of the following ingredients :
- saturated or unsaturated higher organic mono- or polyacids, e.g. sebacic, stearic, linolec, etc.
- organic compound having at least one trivalent nitrogen atom, e.g. nicotinic acid, dipyridyl,$(HOCH_2CH_2)_3N$, etc.
- wetting agents of the alkyl or aryl-sulfonate type; lauryl sodium sulfate, FCGB***, etc.
- optionally, 0.01 to 5 g/l of the following metal ions: Pb, Fe, Se, Hg, Cs, Pd, As, Sb, In, Co.

Au is present as gold sulfite or gold sulfite complexed with an amine, e.g. en.
Cu, Cd, Ni, Zn, Sb are present as water-soluble compounds (mineral or organic acid salts, complex salts, e.g. with en)
en = ethylene diamine, EDTA = ethylene diamine tetracetic acid
* As sulfate;
** adjusted by the addition of alkalis, e.g. $NH_4OH$, NaOH, KOH, etc., or acids, e.g. $H_2SO_4$, $H_3PO_4$, $SO_2$, etc.
⁺tetrasodium salt;
***wetting agent supplied by OXY METAL FINISHING (SUISSE) S.A., Avenches.
⁺⁺disodium salt.

The following Examples illustrate the invention in detailed manner. For achieving the results of these Examples, sulfite baths for the electrodeposition of gold alloys have been prepared and small brass plates tion of hiding originally produced defects (e.g. burns) by the freshly deposited layers of alloy: for instance, it was noted that when burns were intentionally produced by increasing the current density and thereafter the current was reduced to normal (0.5 A/dm²), the burns remained present even at much higher coating thickness. It should also be noted that operating the above bath below 0.5 A/dm² may be inconvenient as the colour of the deposit becomes yellower.

Aliquots of the above control bath were taken and modified by adding in each 0.005 to 0.01 mole/l of one of the organo-phosphorus additives shown in Table 2 below. Then the above plating operations were repeated with each of the modified baths.

The differences resulting from the presence of the additive on the quality of the platings and on the operateing conditions were recorded. The main parameters which were checked were the levelling power defined as above, the surface condition of the deposit (gloss) and the limits of variations of the current density during plating without producing defective coatings.

The results obtained (Examples of compounds 1 to 18) plus control are recorder in Table 2 which also shows the concentration of each of the additives used. The composition of the plated alloy was about 18-19 carat ($\simeq$ 20% Cd and 2-3% Cu).

creasing too much their effect. It the concentration of said additives is increased in the plating baths, their action will be still augmented up to a maximum of efficiency. The concentrations corresponding to this maximum depend strongly on the kind of the additive and on the composition of the bath wherein it is used. In general, because of cost considerations, it is advantageous to operate at concentrations in the neighbourhood of those indicated in Table 2.

The organo-phosphorus additives used in Examples 1 to 18 can be prepared as follows (the temperatures are in degrees Centigrades).

1. Diphosphono-ethyl-hydroxy-methane (1-hydroxypropane-1,1-diphosphonic acid)

Ref.: Belgian Pat. No. 619,619. A mixture of 164 g (2 mole) of orthophosphorus acid ($H_3PO_3$) and 260 g (2.2 mole) of propionic anhydride was heated to 160° C for 2 hrs. Then the mixture was steam distilled until the condensed distillate became neutral. Then the residue was neutralized with aqueous NaOH at pH 8. The residue was diluted with alcohol which resulted in the precipitation of the sodium salt of the title product;

TABLE 2

| EXAMPLE No. | ORGANO-PHOSPHORUS ADDITIVE | CONC. g/l | CURRENT DENSITY INTERVAL | SURFACE CONDITION | LEVELLING ACTION |
|---|---|---|---|---|---|
| 1 | $(HO)_2OP-COH(C_2H_5)-PO(OH)_2 \cdot 6H_2O$ | 2 | $\simeq 1$ | excellent | excellent |
| 2 | $(CH_3O)_2OP-COH(CH_3)-CH_2Cl$ | 1 | $\simeq 1$ | excellent | excellent |
| 3 | $(HO)_2OP-COH(CH_3)-CH_2Cl$ | 0.9 | $\simeq 1$ | good | good |
| 4 | $(HO)_2OP-CHCl_2$ | 0.8 | $\simeq 1$ | good | acceptable |
| 5 | $(CH_3O)_2OP-COCH_3$ | 0.8 | $\simeq 1$ | good | acceptable |
| 6 | $[(HO)_2OP]_2CH_2$ | 0.9 | $\simeq 1$ | good | good |
| 7 | $[(HO)_2OP-CH_2]_2$ | 2 | $\simeq 1$ | good | good |
| 8 | $[(C_2H_5O)_2OP-CH_2]_2$ | 1.5 | $\simeq 1$ | good | good |
| 9 | $(HO)_2OP-(CH_2)_3-PO(OH)_2$ | 1 | $\simeq 1$ | good | good |
| 10 | $(HO)_2OP-CH_2COOH$ | 0.7 | $\simeq 1$ | acceptable | acceptable |
| 11 | $[NaO, H_5C_2O \backslash PO-CH_2]_2 O$ | 1.6 | $\simeq 1$ | acceptable | good |
| 12 | $(H_5C_2O)_2PO-C(OH)(((CH_2)_2OH))-PO(OC_2H_5)_2$ | 1.8 | $\simeq 0.2-0.3$ | acceptable | inferior |
| 13 | $(H_5C_2O)_2PO-CO-(CH_2)_2OH$ | 1 | 0.2-0.3 | inferior | inferior |
| 14 | $(H_5C_2O)_2PO-CONH-C_4H_9$ | 1.3 | 0.2 | acceptable | inferior |
| 15 | $(HO)_2PO(CHOH)_5CH_2OH$ | 1.5 | 0.2-0.3 | acceptable | inferior |
| 16 | $(HO)_2OP-CO-PO(OH)_2$ | 1 | $\simeq 1$ | excellent | excellent |
| 17 | $(HO)_2OP-CCl_2-PO(OH)_2$ | 1.1 | $\simeq 1$ | excellent | excellent |
| 18 | $[H_5C_2O, HO \backslash PO / C(OH)(CH_3)]_2$ | 2 | 1.5-2 | excellent | excellent |
| Control | — | — | <0.1 | poor | none |

As can be seen from the results of Table 2, some of the additives are more active than others. However, it does not appear to be any correlation of the activity with the chemical structure.

The quantities of the additives used in the Examples shown in Table 2 are quite small, however the amount of some of them can be further decreased without decreasing too much their effect.

yield 30 g.

2. and 3. 1-Chloro-2-hydroxy-2-phosphonopropane and its methyl ester

Ref.: C.A. 51, 12878e. 29 g of dimethylphosphite and 24.2 g of chloroacetone were heated together to 120° C for 24 hrs. The ester crystallized by cooling. The crude product was recrystallized from cyclohexane, m.p. 63°–65°; yield 32 g.

The above ester (25 g) was boiled for 8 hrs in a mixture of 25 g conc. HCl and 100 ml of $H_2O$. After cooling, the crude acid separated as a reddish oil which crystallized slowly on standing.

4. Dichloromethanephosphonic acid

Ref.: Lieb. Ann. 679, 51 (1964). A solution of tris-dimethylaminophosphine (16.3 g) in anhydrous ether (100 ml) was added dropwise to 23.8 g of $CHCl_3$ in 500 ml of anh. ether. During the addition, the temperature gradually rose to 45° C. The ether was then evaporated and a solution of 25 ml conc. HCl in 100 ml of $H_2O$ was added to the residue. After boiling for 4 hrs, the mixture was distilled and gave 21 g of the title acid, b.p. 110°–115°/15 mm.

5. Dimethylacetylphosphonate

Ref.: C.A. 41, 88d; 42, 4132i. Trimethyl phosphite (31 g) was added dropwise at −5° C to 19.5 g of acetyl chloride. After standing overnight, the mixture was distilled and gave 18 g of the title ester, b.p. 75°–78°/15 mm.

6. Diphosphonomethane

Ref.: J. Chem. Soc. 1947, 1465. A mixture of diiodomethane (142.5 g, 0.53 mole) and triethylphosphite (157 g, 0.94 mole) was heated progressively from 130° to 150° C, in the course of 5 hrs, in a flask provided with a reflux condenser having an intermediate outlet tube for collecting volatile distillates.

During the heating operation, 30 g of ethyl iodide were collected. The reaction mixture was thereafter distilled and a fraction, b.p. 100°–120°/0.5-1 mm was separated. This fraction which consisted mainly in tetraethylphosphonomethane was hydrolized by boiling 6 hrs in 350 ml of conc. HCl. After elimination of the HCl under reduced pressure, the residue was crystallized in a mixture of acetic acid and water which gave 2.3 g of the title product, m.p. 203°–6°. The product was identified by IR and NMR spectroscopy.

7. and 8. 1,2-Diphosphonoethane and corresponding ethyl ester

Ref.: J. Chem. Soc. 1947, 1465. A mixture of triethylphosphite (157 g, 0.94 mole) and ethylene dibromide (100 g, 0.53 mole) was heated progressively to 150° C (5–6 hrs.) in the apparatus used for preparing the product of Example 6. During the reaction, 65 g of ethyl bromide were collected. At the end of the heating period, the mixture was temporarily heated to 170° C and allowed to cool.

The crude mixture was distilled and gave 66.6 g of the title product tetraethylester, b.p. 140°–8°/0.5-1 mm. 40 g of the above ester were hydrolized by boiling with 400 ml conc. HCl for 6 hrs. After evaporation of the HCl, the residue gave, after crystallization 24 g of the desired acid, m.p. 207°–11°. The structure of the compound was confirmed by IR and NMR spectroscopy.

9. 1,3-diphosphonopropane

Ref.: J. Chem. Soc. 1947, 1465. $(EtO)_3P$ (157 g, 0.94 mole) and 1,3-dibromopropane (107.6 g, 0.53 mole) were treated as described above for 5 hrs at 130°–170° C. Propyl bromide 59.2 g was eliminated and distillation of the residue gave 56.5 g of tetraethyl 1,3-diphosphonopropane, b.p. 156°–165°/0.5-1 mm.

The crude acid (30 g), m.p. 149°–155° was obtained as usual from boiling the above ester for 6 hrs in 600 ml conc. HCl.

10. Phosphonoacetic acid (Hydroxycarbonylmethane phosphonic acid)

Ref.: C.A. 41, 700. Sodium ethoxide (27.2 g, 0.4 mole) was added to a solution of diethylphosphite (55.2 g, 0.4 mole) in 200 ml of anhydrous xylene. While keeping the temperature around 0°–10° C by cooling, ethyl bromoacetate (66.8 g, 0.4 mole) was added dropwise to the above mixture. The NaBr which formed was centrifugated out and the clear liquid was then distilled which gave diethyl ethoxycarbonylmethanephosphonate, b.p. 80°–85°/1 mm.

4.62 g of the above ester were hydrolized by boiling for 20 hrs with 100 ml conc. HCl and gave 0.8 g of the title acid, m.p. 138°–141°. The structure was confirmed by IR and NMR spectroscopy.

11. Di-(phosphonomethyl)-ether

Ref.: C.A. 1943, 3049. Sodium ethoxide (39.44 g, 0.58 mole) was reacted with 74.8 g (0.58 mole) of diethylphosphite in 250 ml of anhydrous xylene. Then, 25 ml (0.29 mole) of di-(chloromethyl)ether was added slowly under cooling. The mixture was heated 3 hrs to 90° C and the NaCl formed was filtered out. Reduced pressure distillation of the clear phase gave 37 g of the tetraethyl ester of the title product.

The above ester was boiled 20 hrs with 300 ml of concentrated HCl. Then, after evaporating the volatile fraction under reduced pressure, the residue was dissolved in 100 ml water, treated with 2 g of active carbon and filtered hot. Then it was neutralized to pH 8 (NaOH) and evaporated. The product which crystallized overnight was shown to be the symmetrical diethylesterdisodium salt of the title acid.

12. Tetraethyl 1.3-dihydroxy-1,1-diphosphenopropane

Ref.: J. Am. Chem. Soc. 78, 4453 (1956). Diethylphosphite (69 g) was slowly added to β-propiolactone (18 g) in the presence of 4 ml of triethylamine as catalyst. During the addition (½ hr), the temperature progressively rose to 100° C. The mixture was stirred for 4 hrs at room temperature then it was left overnight.

After eliminating the excess of diethylphosphite, distillation gave 26 g of the title product, b.p. 130°–133°/15 mm.

13. Diethyl 2-hydroxyethanephosphonate

Ref.: J. Am. Chem. Soc. 78, 4453 (1956). Diethylphosphite (34.5 g) was slowly added while stirring to β-propiolactone (18 g) in the presence, as a catalyst, of 4 ml of triethylamine. In the course of the addition (½ hr), the temperature slowly rose to 125° C. After stirring 4 mere hrs at room temperature, the mixture was left aside overnight.

Then the mixture was distilled and gave, after eliminating unreacted diethylphosphite, 12 g of the above diethylester, b.p. 110°–115°/15 mm. The product was identified by IR and NMR spectroscopic analysis.

14. Diethyl N-butylacetamidophosphonate

Ref.: Canadian Patent No. 509.034. Under strong cooling, butyl isocyanate (25 g) was slowly dropped into a solution of sodium (0.4 g) in diethylphosphite (34.5 g), so as to maintain the temperatue below 5° C. After standing overnight the crystallized product was filtered off; yield 12.5 g, m.p. 32°–33° C.

15. Reaction product of glucose with $H_3PO_3$ 45 g of glucose and 20.5 g of orthophosphorus acid were stirred together for 24 hrs at room temperature in 250 ml $H_2O$. Thereafter, the water was removed by evaporation and the residue washed with alcohol and dried whereby it slowly crystallized. Yield 51 g.

16. and 17. Diphosphono-dichloromethane and diphosphonocarbonyl (esters and Na salts)

Ref.: J. Org. Chem. 32, 4111 (1967). Tetraethyl methanediphosphonate (described hereinabove) was chlorinated or brominated either by the action of the corresponding halogen or by means of the corresponding hypohalogenite. The halogen groups were eliminated by mild alkaline hydrolysis for obtaining the carbonyl diester. Sodium salts of the corresponding acids were prepared according to the above reference.

18.

Ref.: Belgian Pat. No. 619,619. The free acid was prepared according to the method described above in the case of the compound of Example 1. with 82 g (1 mole) of $H_3PO_3$ and 110 g (1.1 mole) of acetic anhydride.

50 g of the pure tetrafunctional acid were boiled for 10 hrs with 500 ml of ethanol. Elimination of the excess alcohol by evaporation gave an oily colourless residue which was titrated with alkali and showed to be a diacid. Analysis confirmed its structure. It was used as such in electroplating baths.

Surprisingly, it was found to be more active as an additive than the corresponding original tetrafunctional acid.

In order to otherwise demonstrate the action of the present organophosphorus additives on sulfite gold and gold alloys electroplating baths, the following experiments were performed:

A bath for the electrodeposition of gold alloys was prepared by dissolving the following ingredients in water:

| Ingredients | Concentration |
|---|---|
| Au (as sulfite) | 4 g/l |
| Ni (as $NiSO_4$ . $6H_2O$ | 12 g/l |
| Cd (as $CdSO_4$) | 10.6 g/l |
| Cu (as DTPA complex) | 0.05 g/l |
| $Na_2SO_3$ | 25 g/l |
| Citric acid | 25 g/l |
| Disodium EUTA . $2H_2O$ | 115 g/l |
| pH (NaOH or $H_2SO_4$) | 9.5 |

0.005 mole/l of some of the above described additives were added to fractions of this bath and the electrolytic polarization curves of the modified baths were measured. These curves represent the correlation between the plating current and the corresponding plating voltage applied between standard reference electrodes. The measurements were performed with the following apparatus: WENKING-68TSI "potentiostat" GERHARD BANK ELEKTRONIK coupled to a function generator (HEWLETT-PACKARD, Model 3310A) and to a precision XY recorder. The variation of applied voltage was a triangular signal having a frequency of $5 \times 10^{116}$ 4 Hz. This signal was swept over about 2 volt in 30 min. The reference electrode was the saturated calomel electrode, ($E_O = 0.2154 \pm 0.006V$ at 60° C). The baths were stirred and three degrees of agitation were available: weak (3 m/min.), medium (7–8 m/min.) and strong (20–21 m/min.). The cathode surface (gilt brass) was 20 cm²; the anode (platinated titanium) was 60 cm². The volume of the solution was 600 ml. The temperature was controlled $\pm 0.1°$ C).

Figure 1:
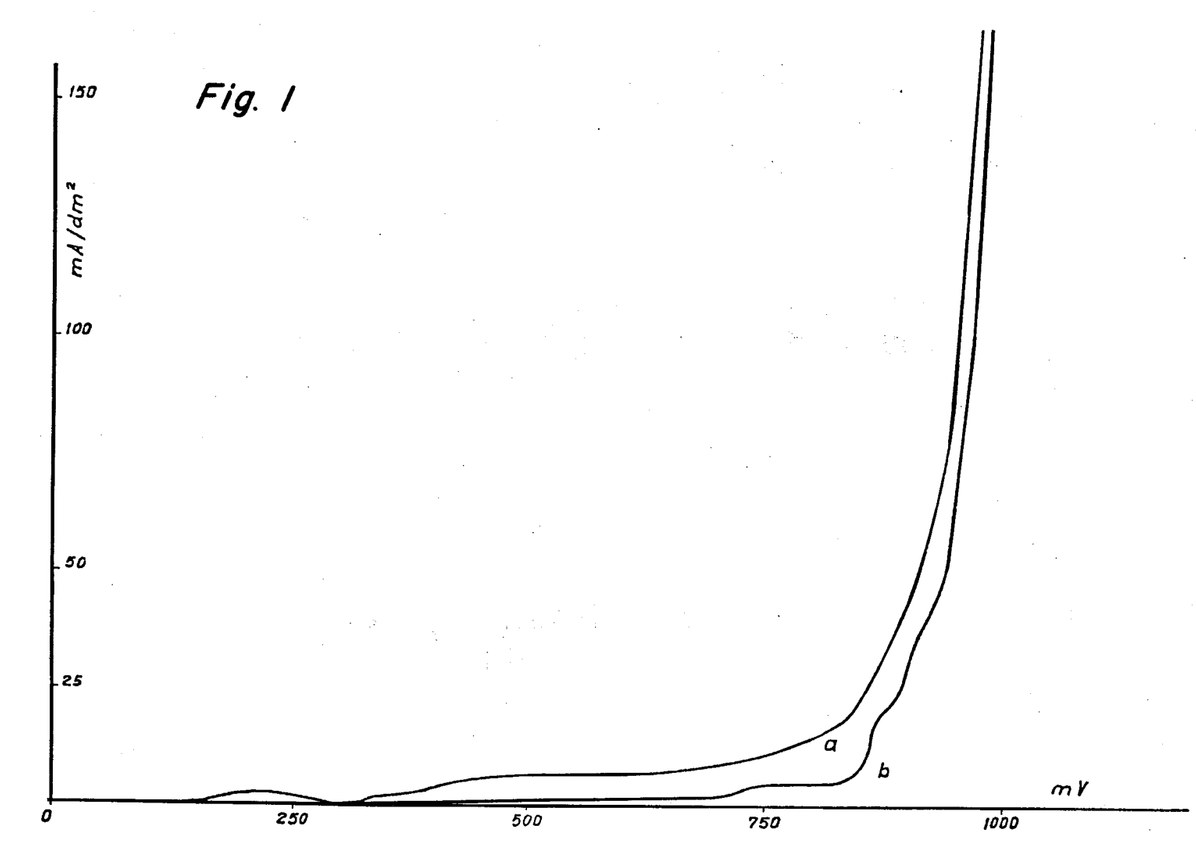
FIG. 1 concerns the additive of Example 1
FIG. 2 concerns the additive of Example 5
FIG. 3 concerns the additive of Example 6
FIG. 4 concerns the additive the Example 12
FIG. 5 concerns the additive of Example 13
FIG. 6 concerns the additive of Example 18
FIG. 7 concerns, for comparative purposes, the tetraacid $(HO)_2PO—C(CH_3)OH—PO(OH)_2$ which corresponds to the additive of Example 18.
Figure 2:
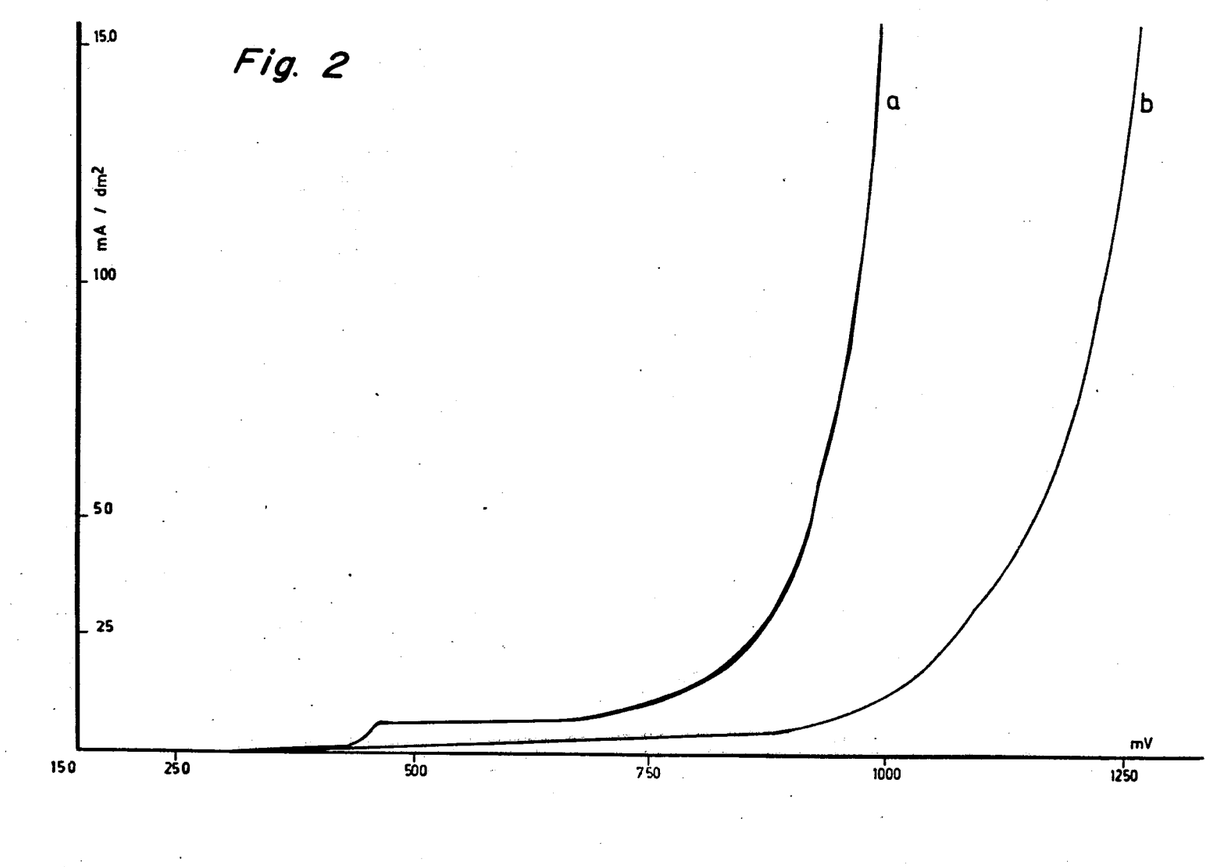
Figure 3:
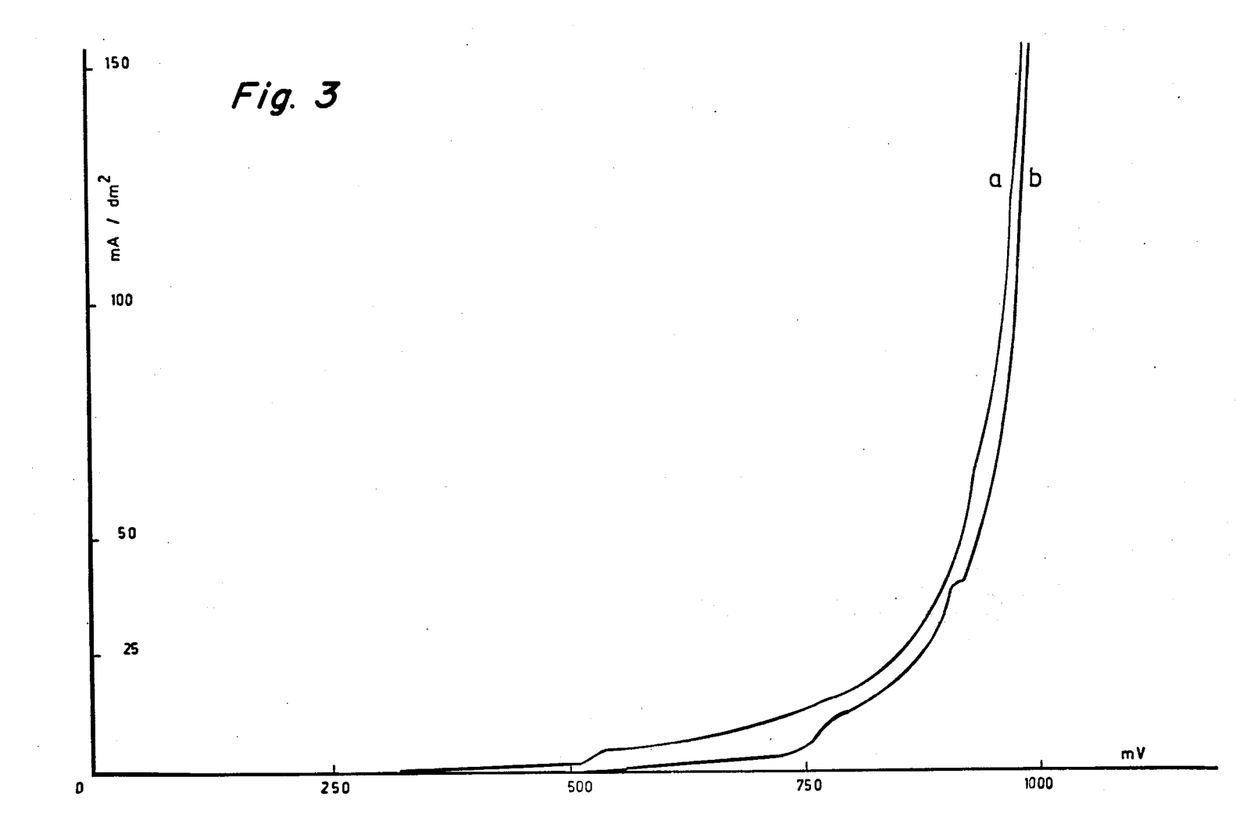
Figure 4:
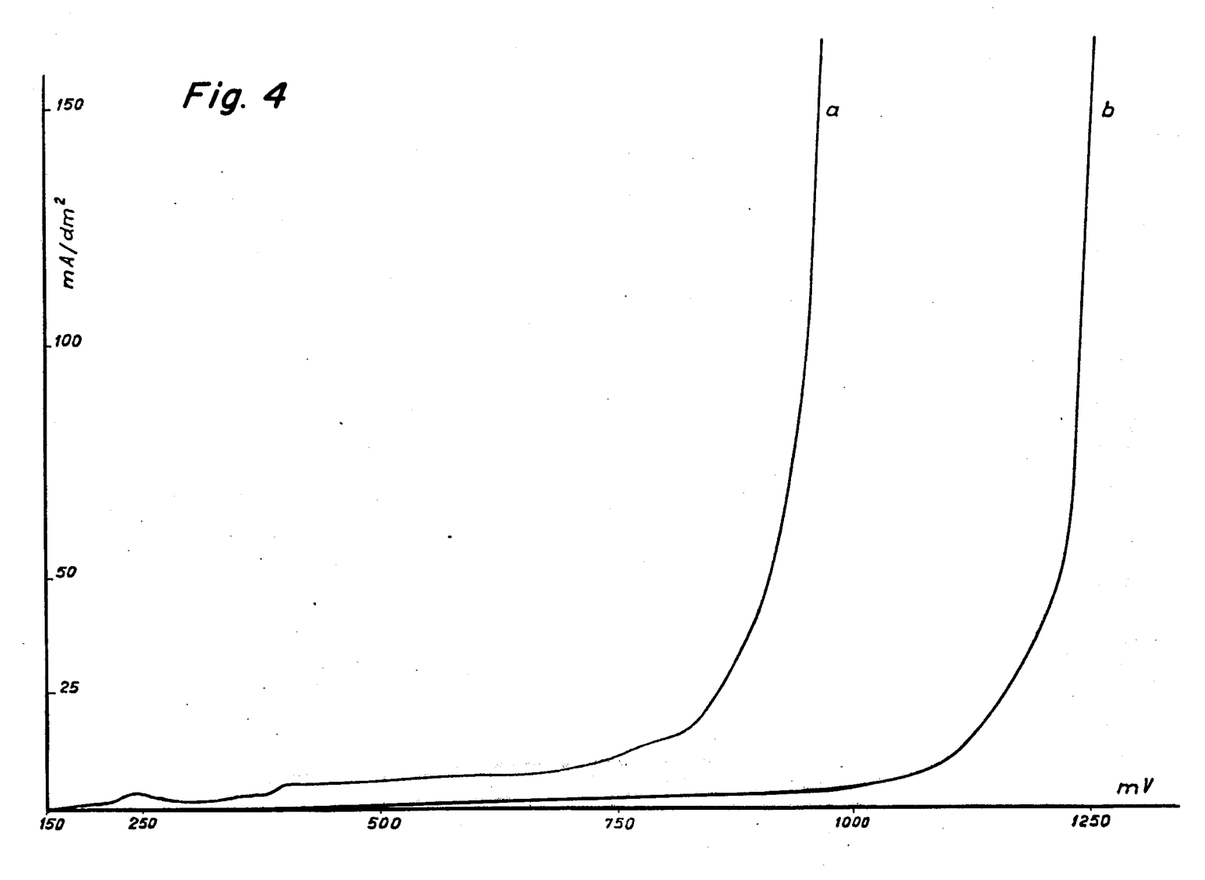
Figure 5:
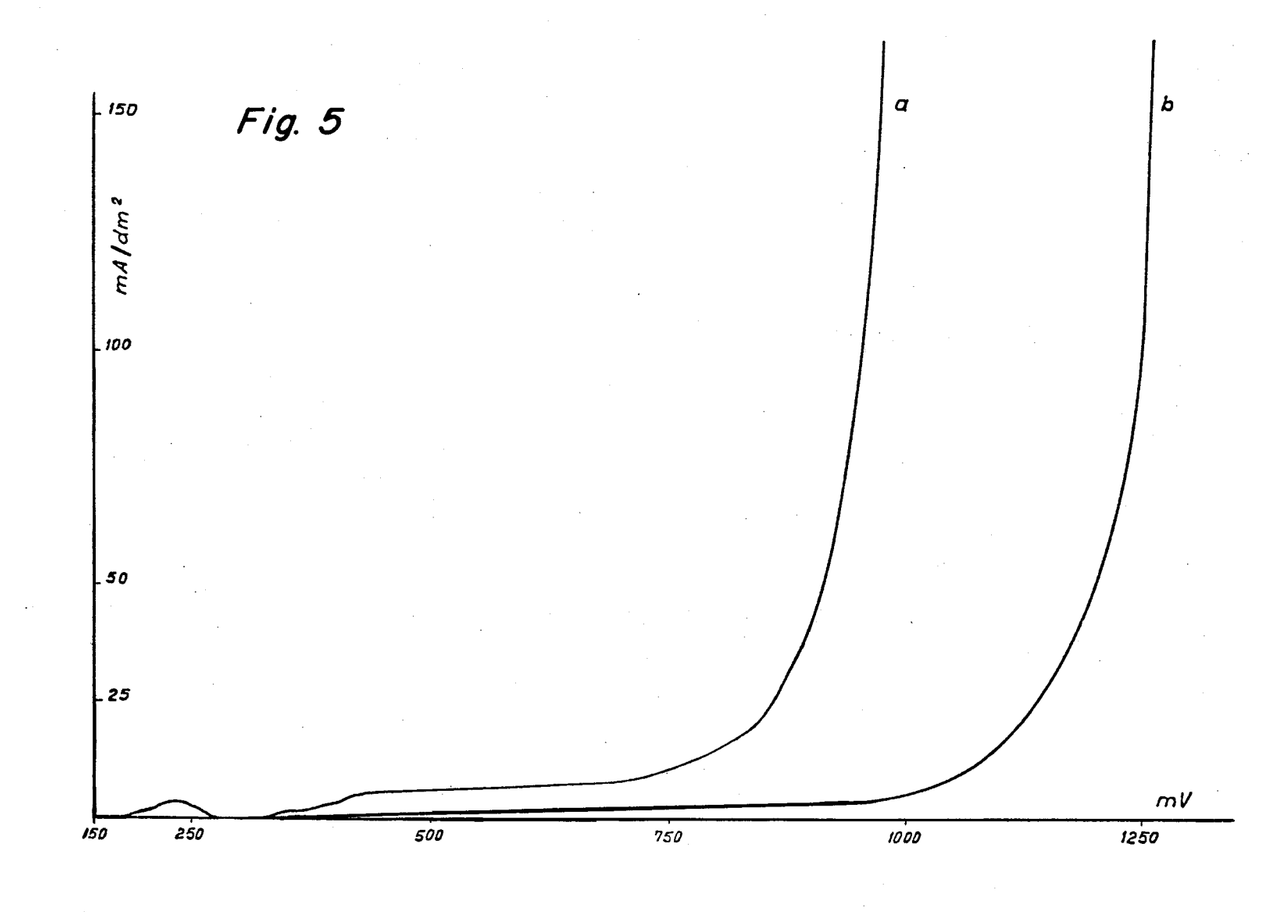
Figure 6:
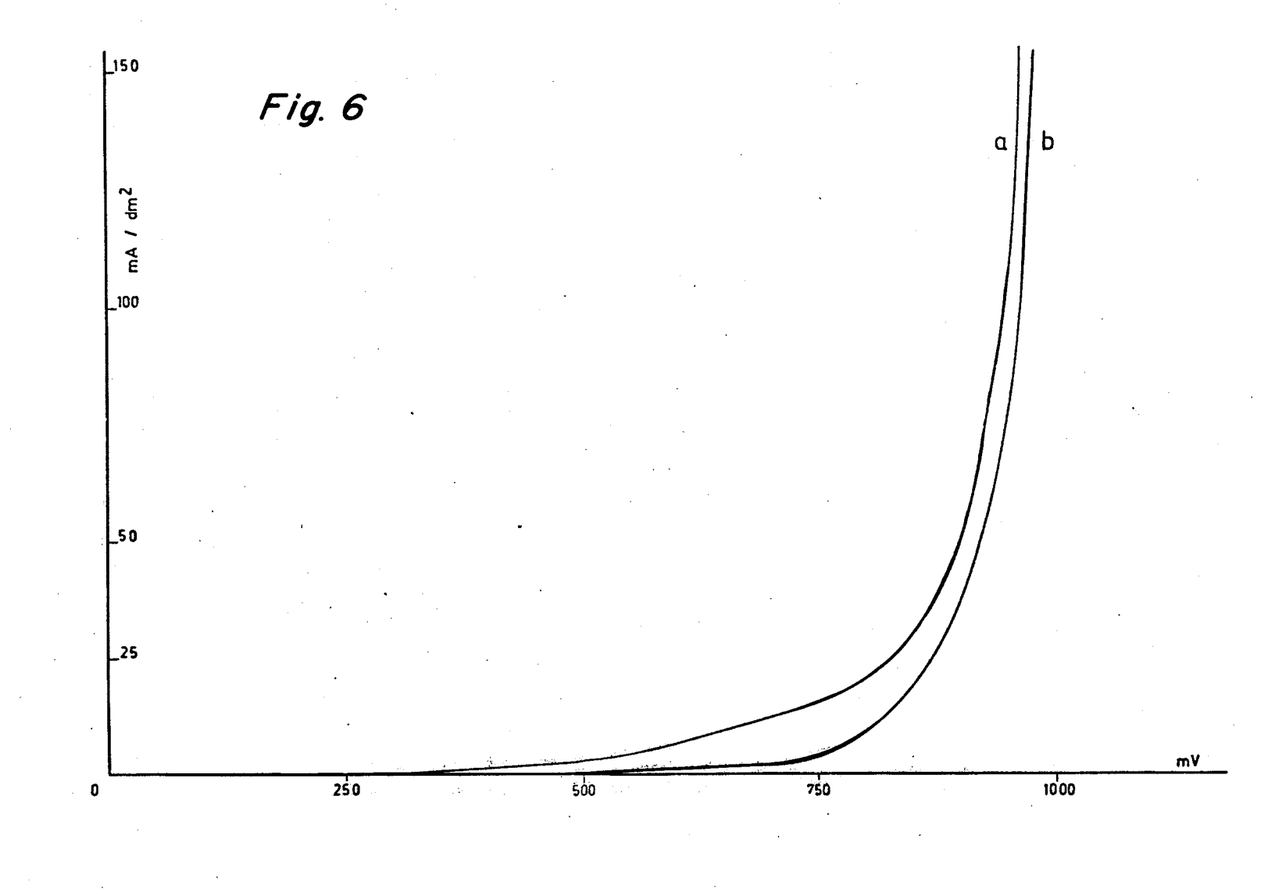
Figure 7:
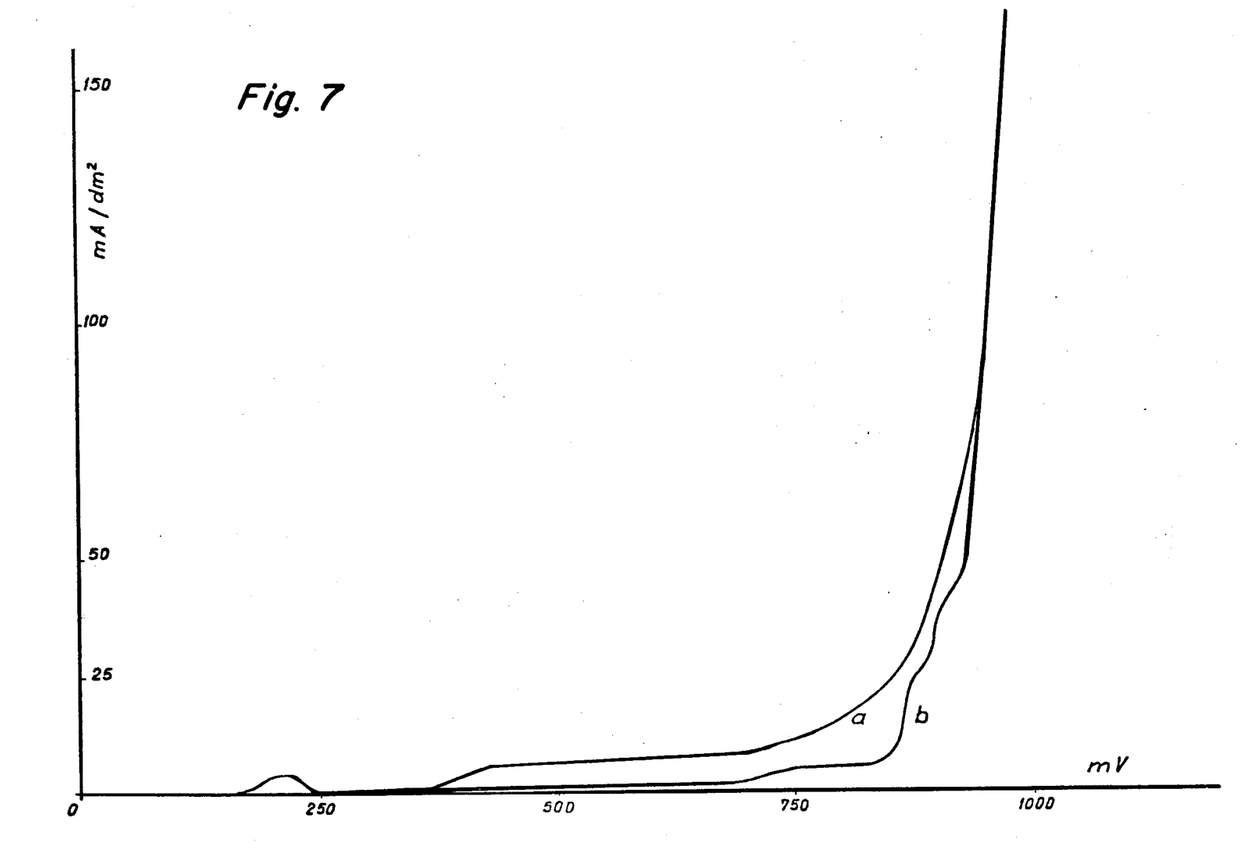

FIGS. 1 to 7 show the results obtained. On each of said FIGS., curve (a) represents the behaviour of the above bath without additives (control); whereas curve (b) expresses the effect of the additive. The position and the shape of these curves indicate that, in general, the effect of the organophosphorus additives is to produce a rightwise displacement of the curve and to make it steeper. This trend correlates with a standardization action on the electrodeposition potentials of the various metals of the plated gold alloy. The composition of this alloy was about 18 carat and about 20 % Cd.

We claim:

1. In an aqueous electroplating bath for the deposition of gold or a gold alloy from a sulfite complex, the improvement comprising including from 1 mg/l up to solubility limit of the bath of a soluble diphosphonic compound of the formula $(HO)_2PO—B—PO(OH)_2$ as a free acid, salified or esterified, wherein B is a linear, branched or cycle containing alkylene or aralkylene hydrocarbon chain of 1 to 30 carbon atoms, saturated or unsaturated, which may be interrupted with a heterofunction selected from the group consisting of -O- and —NH—, and which contains at least one carbonyl or halide substituent.

2. The bath of claim 1 wherein B contains at least one additional constituent selected from the group consisting of hydroxy, carboxy, amino and cyano.

3. The bath of claim 1 wherein B is

4. The bath of claim 1 wherein B is

5. A process for obtaining a gold or gold alloy deposit on a conductive surface comprising immersing the surface in the bath of claim 1 and electrolyzing the bath with the surface as cathode.

* * * * *